United States Patent [19]

Napoletano et al.

[11] Patent Number: 5,142,066
[45] Date of Patent: Aug. 25, 1992

[54] STEREOSELECTIVE PROCESS FOR THE PREPARATION OF 2-AMINO-ETHANOL DERIVATIVES HAVING A CENTRAL ANALGESIC ACTIVITY AND INTERMIDIATES THEREOF

[75] Inventors: Mauro Napoletano, Milan; Gian C. Grancini, Nova Milanese; Carlo Veneziani, Bresso; Dario Chiarino, Monza, all of Italy

[73] Assignee: Zambon Group S.p.A, Vicenza, Italy

[21] Appl. No.: 672,685

[22] Filed: Mar. 20, 1991

[30] Foreign Application Priority Data

Mar. 28, 1990 [IT] Italy ................. 19856 A/90

[51] Int. Cl.$^5$ ............... C07D 207/273; C07D 207/267
[52] U.S. Cl. .................... 548/554; 548/550
[58] Field of Search ............... 548/550, 554

[56] References Cited

U.S. PATENT DOCUMENTS 3,775,431 11/1973 Rodewald et al. ........... 548/554
4,851,547 7/1989 Kita et al. ................... 546/167

FOREIGN PATENT DOCUMENTS 0342613 5/1989 European Pat. Off. .
0322395 6/1989 European Pat. Off. .
0338435 10/1989 European Pat. Off. .
279669 7/1990 German Democratic Rep. .................... 548/550

OTHER PUBLICATIONS

White et al. Tetrahedron 45(21), 6631-6644, 1989.
Vekemans et al. J. Org. Chem., 1987, 52, 1093-1099.

*Primary Examiner*—David B. Springer
*Attorney, Agent, or Firm*—Stevens, Davis, Miller & Mosher

[57] ABSTRACT

A stereoselective process for the preparation of the compounds of formula

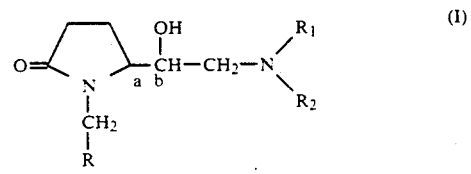

wherein R, $R_1$, $R_2$, a and b have the meanings reported in the specification, is described.

The compounds of formula I have a remarkable central analgesic activity and they are useful in the pharmaceutical field.

6 Claims, No Drawings

STEREOSELECTIVE PROCESS FOR THE PREPARATION OF 2-AMINO-ETHANOL DERIVATIVES HAVING A CENTRAL ANALGESIC ACTIVITY AND INTERMIDIATES THEREOF

The present invention relates to a stereoselective process for the preparation of 2-amino-ethanol derivatives and, more particularly, it relates to a stereoselective process for the preparation of compounds of formula

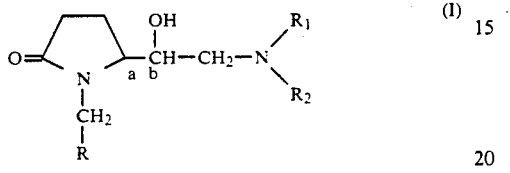

wherein
R is a phenyl optionally substituted by from 1 to 3 substituents selected among $C_1-C_4$ alkyl, $C_1-C_4$ alkoxy, hydroxy, halogen, $CF_3$;
$R_1$ and $R_2$, the same or different, are a linear or branched $C_1-C_6$ alkyl, a $C_3-C_6$ cycloalkyl; or
$R_1$ and $R_2$, together with the nitrogen atom to which they are bonded, make a 5- or 6- membered heterocycle, which can further contain 1 or 2 heteroatoms selected among oxygen, nitrogen and sulfur, optionally substituted by 1 or 2 $C_1-C_4$ alkyl groups;
a and b mark the asymmetric carbon atoms.

The compounds of formula I are described in the European Patent Application No. 0342613 in the name of the same applicant and are useful in the pharmaceutical field as analgesics.

The stereoselective process object of the present invention is reported in the following scheme 1.

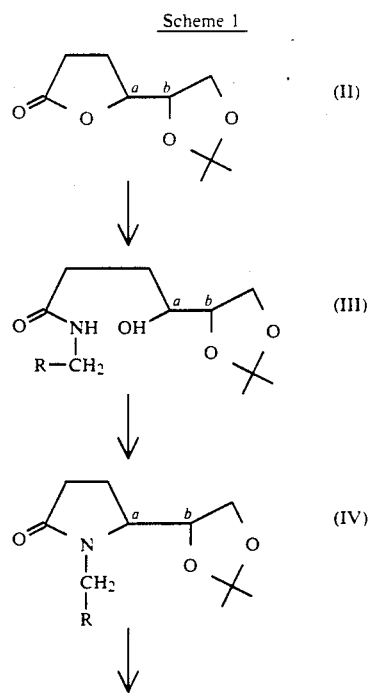

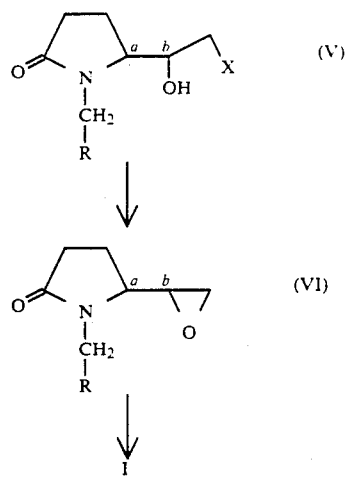

wherein R, a and b have the above reported meanings and X is a hydroxy or a chlorine or bromine atom.

The compounds of formula I have at least two stereogenic centers which have been indicated with a and b.

The stereoselective process object of the present invention allows to obtain any stereoisomer of the compounds of formula I depending on the configuration of the starting compounds of formula II.

The compounds of formula II are known [White J. D. et al., Thetrahedron, 45(21), 6631-44, (1989)] or they are prepared according to known methods.

In fact, the starting compounds II can be prepared by reduction reactions, for example as described in the above reported paper, or by ketalization of the corresponding diol, for example, with acetone.

By using a suitable benzyl amine of formula $RCH_2NH_2$ (VII), wherein R has the above reported meanings, the compound of formula III is obtained starting from the compound of formula II with predetermined configuration at the a and b centers.

The introduction of the benzylamine VII in the compound of formula II does not modify the configuration of the chiral carbon in a. Consequently, in the compound of formula III, the chiral carbon atom a has the same configuration of the starting compound II.

As an example, starting from a compound of formula II in which the carbon atom a has S configuration, a compound of formula III, in which the carbon atom a (corresponding to the atom a of the starting compound II) has S configuration is obtained.

Clearly, the configuration of the chiral carbon atom b remains unchanged.

By cyclization, the compound of formula III is transformed into the compound of formula IV.

The cyclization is carried out by transforming first the hydroxy group in a into a leaving group and then by ring closure of the resulting derivative.

For example, by using methanesulphonyl chloride in a suitable solvent or mixture of solvents (e.g. methylene chloride, chloroform, pyridine) in the presence of a suitable base (e.g. triethylamine, sodium hydroxide) at a temperature comprised between $-20°$ C. and $+80°$ C., the hydroxy group is transformed into the mesyl group. This mesyl derivative can be optionally isolated but preferably it undergoes directly the cyclization.

The cyclization reaction is carried out in dipolar aprotic solvents e.g. dimethylformamide, dimethoxyethane or dimethylsulfoxide in the presence of sodium hydroxide or sodium hydride.

By the cyclization reaction the configuration of the carbon atom a is inverted while the configuration of the carbon atom b remains the same.

It is clear to the man skilled in the art that an inversion as well as a retention in the configuration of a carbon atom does not necessarily correspond to an inversion or to a retention in the R or S nomenclature respectively. In fact the R or S configuration of a carbon atom depends on the priority order of the different substituents according to a sequence rule procedure (see IUPAC—Nomenclature of organic chemistry—1979 Edition—Pergamon Press, pages 486–90).

The hydrolysis of the compound of formula IV with hydrobromic or hydrochloric acid and acetic acid, in a suitable solvent or mixture of solvents (e.g. methanol, ethanol, isopropanol), gives the halohydrin of formula V (in which X=Br, Cl), which has the same configuration in a and b of the starting compound IV.

The compound of formula V is then transformed into the corresponding epoxide VI by treatment for example with sodium hydride in dimethylformamide.

The reaction between the epoxide of formula VI and an amine of formula $NHR_1R_2$ (VIII) (in which $R_1$ and $R_2$ have the above reported meanings) in a molar ratio 1:1 (or with a slight excess of the amine) gives the compounds of formula I.

The reaction is carried out in a suitable solvent or mixture of solvents such as, for example, t.butyl alcohol, methanol, ethanol. Alternatively, the compound of formula V is directly treated with a large excess of amine VIII (at least a molar amount double with respect to that of compound V) in order to obtain the compounds of formula I. The reaction is carried out in a suitable solvent such as alcohols and dimethylformamide or mixtures thereof.

The compounds of formula VI and I do not modify the configuration of the sterogenic centers a and b which consequently have the same configuration of the starting compound of formula V (X=Br,Cl).

Alternatively the hydrolysis reaction of the compound of formula IV may be carried out with acids in a suitable solvent or mixture of solvents in order to obtain the compounds of formula V in which X=OH.

The thus obtained diol is transformed into the compounds of formula I as already described in the above cited European Patent Application No. 0342613.

Also in this case the carbon atom a and b retain their configuration during the transformation reactions of compound IV to compound V (X=OH) and to compound of formula I.

The compounds of formula III and IV are new and they are a further object of the present invention. Their particular structure allows to realize the above described stereoselective process.

The availability of the four stereoisomers of compound II allows to prepare the compounds of formula I with any possible configuration at carbon atoms a and b.

For example, starting from the compound of formula II with R configuration in a and S configuration in b, the compounds of formula I in which a and b are contemporaneously S are obtained.

On the contrary, starting from the compound of formula II with S configuration in a and R configuration in b, the compounds of formula I in which a and b are contemporaneously R are obtained.

Otherwise, starting from the compound of formula II in which both a and b are in R configuration, the compounds of formula I in which a has S configuration and b has R configuration are obtained and starting from the compound of formula II in which both a and b are in S configuration, the compounds of formula I in which a has R configuration and b has S configuration are obtained.

It is worth underlining that in the process object of the present invention only the configuration of the carbon atom a is inverted. Furthermore it is clear to the man skilled in the art that a suitable ketone for the protection of the hydroxy groups in the compound of formula II can be of different nature from acetone.

In fact, it is within the scope of the present invention the use of other symmetrical ketones, such as for example cyclohexanone and diethylketone, as ketalization agents.

The process object of the present invention comprises highly stereospecific reactions which give intermediates and products with high purity and high chemical yield. Moreover, the versatility of the process object of the present invention, allows to prepare compounds of formula I in any predetermined configuration and enantiomerically pure.

With the aim at better illustrating the present invention the following examples are now given.

EXAMPLE 1

2-iodo-2,3-dideoxy-5,6-O-isopropylidene-L-lyxo-hexono-1,4-lactone (Compound No. 1)

A solution of 3-deoxy-5,6-O-isopropylidene-2-O-mesyl-L-xylo-hexono-1,4-lactone (1.18 g; 4.21 mmol) and sodium iodide (0.95 g; 6.31 mmol) in acetone (10 ml) was refluxed for 90 minutes.

The reaction mixture was cooled, diluted with water (50 ml) and extracted with ethyl acetate (2×20 ml). The organic phase was washed with an aqueous solution of sodium metabisulfite (10 ml), water (10 ml), dried on sodium sulfate and evaporated.

Compound No. 1 (1.2 g) was obtained as a yellow solid.

m.p. 101°–103° C.

$[\alpha]^{20}_D = -15.4°$ (c=1.8%-CHCl$_3$)

$^1$H-NMR (200 MHz, DMSO-d$_6$): δ (ppm): 4.81–4.76 (m, 1H); 4.61–4.52 (m, 1H); 4.25–4.17 (m, 1H); 4.05–3.75 (m, 2H); 2.59–2.30 (m, 2H); 1.30 (s, 3H); 1.27 (s, 3H).

By working in a similar way the following compound was prepared:

2-iodo-2,3-dideoxy-5,6-O-isopropylidene-D-lyxo-hexono-1,4-lactone (Compound No. 2)

starting from 3-deoxy-5,6-O-isopropylidene-2-O-mesyl-D-xylo-hexono-1,4-lactone

90% yield m.p. 102°–103° C.

$[\alpha]^{20}_D = +15.2°$ (c=1.8%-CHCl$_3$)

$^1$H-NMR analogous to that described for compound No. 1.

EXAMPLE 2

(4S,5S)-4,5,6-trihydroxy-5,6-O-isopropylidene-hexanoic acid-1,4-lactone (Compound No. 3)

A solution of compound No. 1 (21.60 g; 69.2 mmol) and triethylamine (14.04 g; 138.7 mmol) in ethyl acetate (267 ml) was hydrogenated at 4 atmospheres in a Parr hydrogenator in the presence of palladium on charcoal at 10% (2.67 g) for 48 hours.

The catalyst was removed by filtration and the organic solution was washed with a saturated aqueous sodium chloride solution (3×50 ml).

The organic phase was dried on sodium sulfate and evaporated at reduced pressure.

Compound No. 3 (11.8 g) was obtained as a brown oil.

$^1$H-NMR (200 MHz, DMSO-d$_6$): δ (ppm): 4.55–4.46 (m, 1H, OCOCH); 4.20–4.11 (m, 1H, OCOCH-CH); $v_A$=4.01 −$v_B$=3.70 (AB portion of an ABX system; $J_{AB}$=8.2 Hz, $J_{AX}$=6.9 Hz, $J_{BX}$=6.4 Hz, OCH-CH$_2$O); 2.50–2.41 (m, 2H, OCOCH$_2$); 2.31–1.83 (m, 2H, OCOCH$_2$—CH$_2$); 1.28 (s, 3H, CH$_3$); 1.26 (s, 3H, —CH$_3$).

By working in a similar way the following compound was prepared:

(4R,5R)-4,5,6-trihydroxy-5,6-O-isopropylidene-hexanoic acid-1,4-lactone (Compound No. 4)

starting from compound No. 2
91% yield-dark oil
$^1$H-NMR analogous to that described for compound No. 3.

EXAMPLE 3

(4S,5S)-4,5,6-trihydroxy-5,6-O-isopropylidene-hexanoic acid-1,4-lactone (Compound No. 3)

A solution of 2,3-dideoxy-5,6-O-isopropylidene-L-threo-2-hexenono-1,4-lactone (1.50 g; 8.1 mmol) in ethyl acetate (30 ml) was hydrogenated at room pressure in the presence of palladium on charcoal at 10% (0.1 g) until theoretical absorption. The catalyst was removed by filtration and the solution was evaporated at reduced pressure.

Compound No. 3 (1.45 g) was obtained as a colorless oil.

$^1$H-NMR analogous to that described in example 2.

By working in a similar way the following compound was prepared:

(4S,5R)-4,5,6-trihydroxy-5,6-O-isopropylidene-hexanoic acid-1,4-lactone (Compound No. 5)

starting from 2,3-dideoxy-5,6-isopropylidene-D-erythro-2-hexenono-1,4-lactone
94% yield-colorless oil which solidifies at 4° C.
$[α]^{20}_D$= +5.3° (c=5%-CHCl$_3$)
$^1$H-NMR (200 MHz, DMSO): δ (ppm): 4.55–4.46 (m, 1H); 4.27–4.18 (m, 1H); 4.07–3.65 (m, 2H); 2.52–2.44 (m, 2H); 2.31–1.90 (m, 2H); 2.42 (s, 3H); 1.27 (s, 3H).

EXAMPLE 4

2,3-dideoxy-L-erythro-hexono-1,4-lactone (Compound No. 6)

Potassium hydroxide (titer 85%; 52.81 g; 800 mmol) was added to a solution of 6-bromo-2,3,6-trideoxy-D-erythro-hexono-1,4-lactone (45.4 g; 217.2 mmol) [I. Lundt et al., Synthesis, 1052–1054, (1986)] in water (791 ml) under stirring at room temperature.

The solution was stirred overnight at room temperature then it was acidified with an aqueous hydrochloric acid solution at 36% (121 ml) and the solvent was evaporated.

The solid residue was collected with acetonitrile (250 ml) and the inorganic solid residue was filtered.

The organic solution was evaporated at reduced pressure.

Compound No. 6 (31.5 g) was obtained as a brown oil.

$[α]^{20}_D$= −4.4° (c=2%-methanol)
$^1$H-NMR (200 MHz, DMSO): δ (ppm): 5.11 (d, 1H, $J_{HH}$=5.3 Hz); 4.70 (t, 1H, $J_{HH}$=5.7 Hz); 4.57–4.48 (m, 1H); 3.71–3.60 (m, 1H); 3.42–3.25 (m, 2H); 2.47–2.02 (m, 2H).

EXAMPLE 5

(4R,5S)-4,5,6-trihydroxy-5,6-O-isopropylidene-hexanoic acid-1,4-lactone (Compound No. 7)

Isopropenyl-methyl-ether (18.8 g; 260 mmol) was added dropwise to a solution of compound No. 6 (29.23 g; 200 mmol) and p.toluenesulfonic acid monohydrate (0.321 g) in dimethylformamide (200 ml) under stirring at 4° C.

At the end of the addition, the solution was stirred at room temperature for 18 hours then sodium carbonate decahydrate (20 g) was added.

The solution was left under stirring for 30 minutes.

The solid was filtered and the solution was evaporated at reduced pressure at 50° C. The residue was collected with ethyl acetate (300 ml) and washed with water (3×50 ml).

The organic phase was dried with sodium sulfate and evaporated.

Compound No. 7 (32 g) was obtained as a colorless oil which solidifies at 5° C.

$[α]^{20}_D$= −5.3° (c=5%-chloroform)
$^1$H-NMR analogous to that described for compound No. 5.

EXAMPLE 6

6-bromo-2,3,6-trideoxy-L-erythro-hexono-1,4-lactone (Compound No. 8)

A solution of compound No. 6 (1.03 g; 7.05 mmol) in hydrobromic acid at 37% in acetic acid (10 ml) was stirred at room temperature for 3 hours.

Methanol (16 ml) was added and the stirring was continued for 20 hours.

The solvent was evaporated and the residue was collected with water (10 ml) and evaporated to dryness.

The residue was collected with chloroform (15 ml) and treated with sodium bicarbonate (1.0 g) under stirring.

The solid was filtered and the solution was evaporated to dryness at reduced pressure.

Compound No. 8 (1.27 g) was obtained as a white solid.

m.p. 76°–77° C.
$[α]^{20}_D$= −20.1° (c=5%-chloroform)
$^1$H-NMR (200 MHz, DMSO-d$_6$): δ (ppm): 5.76 (broad, d, 1H, $J_{HH}$=6 Hz, OH); 4.53–4.43 (m, 1H, COOCH); 3.84–3.74 (m, 1H, CH-OH); 3.58–3.37 (m, 2H, CH$_2$—Br); 2.51–2.42 (m, 2H, OCOCH$_2$); 2.25–1.98 (m, 2H, OCOCH$_2$—CH$_2$).

An $^1$H-NMR test carried out in the presence of a chiral shift-reagent [10 mg of compound No. 8 in deuterochloroform (0.6 ml) in the presence of Europhium (hfc)$_3$] confirmed the absence of the 6-bromo-2,3,6-trideoxy-D-erythro-hexono-1,4-lactone enantiomer).

EXAMPLE 7

2,3-dideoxy-D-erythro-hexono-1,4-lactone (Compound No. 9)

It was prepared as described in example 4 starting from compound No. 8.
98% yield-oil
$[\alpha]^{20}_D = +4.3°$ (c=2%-methanol)
$^1$H-NMR analogous to that described for compound No. 6.

EXAMPLE 8

(4S,5R)-4,5,6-trihydroxy-5,6-O-isopropylidene-hexanoic acid-1,4-lactone (Compound No. 5)

It was prepared as described in example 5 starting from compound No. 9.
82% yield-colorless oil which solidifies at 5° C.
$[\alpha]^{20}_D = +5.4°$ (c=5%-chloroform)
$^1$H-NMR analogous to that described in example 3.

EXAMPLE 9

(4S,5S)-N-(2-chlorobenzyl)-5,6-O-isopropylidene-4,5,6-trihydroxyhexanamide (Compound No. 10)

A mixture of compound No. 3 (5.03 g; 27 mmol) and 2-chlorobenzylamine (4.21 g; 30 mmol) was heated at 105° C. for 6 hours.

The residue was dissolved in acetone and chromatographycally purified on silica column (400 g; eluent hexane:acetone=7:3).

Compound No. 10 (8.85 g) was obtained as a white solid.
m.p. 65°-67° C.
$^1$H-NMR (200 MHz, DMSO-d$_6$): δ (ppm): 8.40-8.32 (m, 1H); 7.59-7.25 (m, 4H); 4.31 (d, 2H, $J_{HH}$=6 Hz); 3.92-3.87 (m, 2H); 3.68-3.22 (m, 2H); 2.40-2.15 (m, 2H); 1.80-1.40 (m, 2H); 1.31 (s, 3H); 1.28 (s, 3H).

By working in a similar way the following compound was prepared:

(4R,5R)-N-(2-chlorobenzyl)-5,6-O-isopropylidene-4,5,6-trihydroxyhexanamide (Compound No. 11)

starting from compound No. 4
97% yield-white solid
m.p. 65°-66° C.
$^1$H-NMR analogous to that described for compound No. 10.

EXAMPLE 10

(4R,5S)-N-(2-chlorobenzyl)-5,6-O-isopropylidene-4,5,6-trihydroxyhexanamide (Compound No. 12)

A mixture of compound No. 7 (32.0 g; 172 mmol) and 2-chlorobenzylamine (25.06 g; 177 mmol) was heated at 105° C. for 24 hours.

The mixture was cooled and the solid residue was crystallized from methylisopropylether (850 ml).

Compound No. 12 (50.0 g) was obtained as a white solid.
m.p. 75°-76° C.
$[\alpha]^{20}_D = -10.3°$ (c=5%-chloroform)
$^1$H-NMR (200 MHz, DMSO): δ (ppm): 8.35 (t, 1H, $J_{HH}$=5.5 Hz); 7.46-7.21 (m, 4H); 4.90 (broad signal, 1H); 4.31 (d, 2H, $J_{HH}$=6 Hz); 4.00-3.90 (m, 1H); 3.82-3.71 (m, 2H); 3.37-3.28 (m, 1H); 2.42-2.16 (m, 2H); 1.94-1.36 (m, 2H); 1.29 (s, 3H);

By working in a similar way the following compound was prepared:

(4S,5R)-N-(2-chlorobenzyl)-5,6-O-isopropylidene-4,5,6-trihydroxyhexanamide (Compound No. 13)

starting from compound No. 5
85% yield-white solid
m.p. 75°-76° C.
$[\alpha]^{20}_D = +10.1°$ (c=5%-chloroform)
$^1$H-NMR analogous to that described for compound No. 12.

EXAMPLE 11

(4R,5S)-N-benzyl-5,6-O-isopropylidene-4,5,6-trihydroxyhexanamide (Compound No. 14)

A mixture of compound No. 7 (16.0 g; 86 mmol) and benzylamine (10.7 g; 100 mmol) was heated at 105° C. for 6 hours.

The residue was crystallized from ethylacetate (100 ml).

Compound No. 14 (22.4 g) was obtained as a white solid.
m.p. 78°-79° C.
$[\alpha]^{20}_D = -14.8°$ (c=3%-chloroform)
$^1$H-NMR (200 MHz, DMSO-d$_6$): δ (ppm): 8.3 (t, 1H, $J_{HH}$=6 Hz); 6.35-7.17 (m, 5H); 4.90 (d, 1H, $J_{HH}$=5.9 Hz, OH); 4.25 (d, 2H, $J_{HH}$=6 Hz); 4.02-3.70 (m, 3H); 3.37-3.25 (m, 1H); 3.39-2.12 (m, 2H); 1.93-1.76 (m, 1H); 1.60-1.34 (m, 1H); 1.30 (s, 3H); 1.24 (s, 3H).

By working in a similar way the following compound was prepared:

(4R,5S)-N-(2-methoxybenzyl)-5,6-O-isopropylidene-4,5,6-trihydroxyhexanamide (Compound No. 15)

starting from compound No. 7 and 2-methoxy-benzylamine
81% yield-white solid
m.p. 79°-81° C. (isopropanol-isopropylether)
$[\alpha]^{20}_D = -15.3°$ (c=5%-chloroform)
$^1$H-NMR (200 MHz, DMSO); δ (ppm): 8.13 (t, 1H, $J_{HH}$=5.8 Hz, NH);
7.26-6.84 (m, 4H, Ar); 4.91 (d, 1H, $J_{HH}$=5.8 Hz, OH); 4.20 (d, 2H, $J_{HH}$=5.8 Hz, CH$_2$—NH); 3.98-3.70 (m, OCH—CH$_2$O); 3.80 (s, 3H, Ar—OCH$_3$); 3.37-3.25 (m, 1H, CH—OH); 2.40-2.13 (m, 2H, CH$_2$CO); 1.92-1.33 (m, 2H, COCH$_2$—CH$_2$CH); 1.28 (s, 3H, CH$_3$O); 1.26 (s, 3H, CH$_3$O).

EXAMPLE 12

1-(R)-[1-(2-chlorobenzyl)-2-oxo-5-(R)-pyrrolidinyl]-1,2-isopropylidene-ethanediol (Compound No. 16)

A solution of methanesulfonyl chloride (0.248 g; 2.2 mmol) in methylene chloride (2 ml) was added dropwise to a solution of compound No. 10 (0.503 g; 1.5 mmol) and triethylamine (0.240 g; 2.3 mmol) in methylene chloride (10 ml) under stirring at −10° C.

After an hour the solvent was removed at reduced pressure and dimethylsulfoxide (6 ml) and potassium hydroxide (0.705 g; 12.6 mmol) were added.

The solution was stirred at room temperature for two hours then it was diluted with water (30 ml) and extracted with ethyl ether (3×20 ml).

The organic phase was washed with water (30 ml), dried and evaporated at reduced pressure.

Compound No. 16 (0.40 g) was obtained as a thick oil.
$^1$H-NMR (200 MHz, DMSO-d$_6$): δ (ppm): 7.50-7.20 (m, 4H); 4.78-4.27 (m, 2H); 4.40-4.30 (m, 1H); 3.98-3.48 (m, 2H); 3.68-3.60 (m, 1H); 2.41-1.80 (m, 4H); 1.35 (s, 3H); 1.21 (s, 3H).

EXAMPLE 13

1-(R)-[1-(2-chlorobenzyl)-2-oxo-5-(R)-pyrrolidinyl]-1,2-ethanediol (Compound No. 17)

A solution of compound No. 16 (0.7 g; 2.26 mmol) in a 6N solution of hydrochloric acid in isopropanol (7 ml) was stirred at room temperature for two hours.

The solvent was evaporated at reduced pressure and the residue was crystallized from ethyl acetate (5 ml).

Compound No. 17 (0.6 g) was obtained as a white solid.

m.p. 112°–114° C.

$[\alpha]^{20}_D = -56.0°$ (c=2%-ethanol)

$^1$H-NMR (200 MHz, CDCl$_3$): δ (ppm): 7.34–7.13 (m, 4H); 5.04–4.25 (m, 2H); 4.10–4.00 (m, 2H); 3.56–3.40 (m, 3H); 2.62–1.80 (m, 5H).

EXAMPLE 14

1-(S)-[1-(2-chlorobenzyl)-2-oxo-5-(S)-pyrrolidinyl]-1,2-isopropylidene-ethanediol (Compound No. 18)

A solution of methanesulfonyl chloride (0.259 g; 2.3 mmol) in methylene chloride (2 ml) was added dropwise under stirring at −10° C. to a solution of compound No. 11 (0.525 g; 1.6 mmol) and triethylamine (0.243 g; 2.4 mmol) in methylene chloride (10 ml).

After an hour the organic solution was washed with water (15 ml) and with an aqueous sodium bicarbonate solution at 5% (10 ml), dried on sodium sulfate and evaporated at reduced pressure.

The residue (0.71 g) was collected with dimethylformamide (10 ml), cooled at 0° C. and treated under stirring with sodium hydride 80% in oil (0.077 g; 2.6 mmol).

After 2 hours, the mixture was poured into water (50 ml) and extracted with ether (2×10 ml). The organic phase was washed with water (10 ml), dried on sodium sulfate and evaporated at reduced pressure.

Compound No. 18 (0.48 g) was obtained as a thick oil.

$^1$H-NMR analogous to that described for compound No. 16.

EXAMPLE 15

1-(S)-[1-(2-chlorobenzyl)-2-oxo-5-(S)-pyrrolidinyl]-1,2-ethanediol (Compound No. 19)

It was prepared as described in example 13 starting from compound No. 18.

91% yield-white solid m.p. 112°–113° C.

$[\alpha]^{20}_D = +56.4°$ (c=2%-ethanol)

$^1$H-NMR analogous to that described for compound No. 17.

EXAMPLE 16

(4R,5S)-N-(2-chlorobenzyl)-4-methanesulfonyloxy-5,6-O-isopropylidene-5,6-dihydroxy-hexanamide (Compound No. 20)

A solution of methanesulfonyl chloride (36.4 g; 318 mmol) in methylene chloride (80 ml) was added dropwise under stirring at −10° C. to a solution of compound No. 12 (73.9 g; 225 mmol) and triethylamine (41.5 g; 410 mmol) in methylene chloride (740 ml).

After an hour the organic solution was washed with water (300 ml) and with an aqueous sodium bicarbonate solution at 5% (200 ml).

It was dried on sodium sulfate at reduced pressure.

Compound No. 20 (91 g) was obtained as a light yellow oil which was used for the subsequent step without further purification.

$^1$H-NMR (200 MHz, CDCl$_3$): δ (ppm): 7.41–7.28 (m, 4H); 6.11 (m, 1H); 4.81–4.32 (m, 1H); 4.60–4.40 (m, 2H); 4.24–4.13 (m, 1H); 4.08–3.80 (m, 2H); 3.05 (s, 3H); 2.45–2.37 (m, 2H); 2.20–1.74 (m, 2H); 1.40 (s, 3H); 1.31 (s, 3H).

EXAMPLE 17

1-(R)-[1-(2-chlorobenzyl)-2-oxo-5-(S)-pyrrolidinyl]-1,2-isopropylidene-ethanediol (Compound No. 21)

A solution of compound No. 20 (91 g; 225 mmol) in dimethoxyethane (300 ml) was added dropwise to a suspension of powdered NaOH (45.1 g; 1.13 mmol) in dimethoxyethane (462 ml) under stirring at room temperature.

The suspension was stirred at room temperature for 18 hours, the solid was filtered and the organic solution was evaporated at reduced pressure.

The residue was collected with ethyl ether (400 ml), washed with water (2×100 ml), dried on sodium sulfate and evaporated at reduced pressure.

Compound No. 21 (65.1 g) was obtained as a yellow oil.

$^1$H-NMR (200 MHz, DMSO-d$_6$): δ (ppm): 7.48–7.12 (m, 4H); 4.80–4.50 (m, 2H); 4.12–3.92 (m, 2H); 3.60–3.43 (m, 2H); 2.41–2.00 (m, 3H); 1.68–1.50 (m, 1H); 1.18 (s, 3H); 1.13 (s, 3H).

EXAMPLE 18

1-(R)-[1-(2-chlorobenzyl)-2-oxo-5-(S)-pyrrolidinyl]-1,2-ethanediol (Compound No. 22)

It was prepared as described in example 13 starting from compound No. 21.

92% yield-white solid m.p. 115°–116° C.

$[\alpha]^{20}_D = +53.2°$ (c=1%-ethanol)

$^1$H-NMR (200 MHz, DMSO-d$_6$): δ (ppm): 7.46–7.15 (m, 4H); 4.92 (d, 1H, $J_{HH}$=4.8 Hz); 4.41–4.82 (m, 2H); 4.60 (t, 1H, $J_{HH}$=5.3 Hz); 3.64–3.50 (m, 2H); 3.38–3.33 (m, 2H); 2.43–2.81 (m, 4H).

EXAMPLE 19

1-(S)-[1-(2-chlorobenzyl)-2-oxo-5-(R)-pyrrolidinyl]-1,2-ethanediol (Compound No. 23)

It was prepared as described in examples 16, 17, 18 for the relative enantiomer starting from compound No. 13.

80% yield-white solid $[\alpha]^{20}_D = -53.0°$ (c=1%-ethanol)

$^1$H-NMR analogous to that described for compound No. 22.

EXAMPLE 20

1-(R)-[1-(2-chlorobenzyl)-2-oxo-5-(S)-pyrrolidinyl]-2-bromo-ethanol (Compound No. 24)

A suspension of compound No. 21 (65.1 g; 210 mmol) in hydrobromic acid at 37% in acetic acid (318 ml) was stirred at room temperature for 18 hours.

Then methanol (637 ml) was added and the stirring was continued for 24 hours.

The reaction mixture was evaporated at reduced pressure.

The residue was dissolved in ethyl ether (400 ml), washed with water (2×150 ml), dried on sodium sulfate and evaporated at reduced pressure.

Compound No. 24 (64.3 g) was obtained as a light yellow oil which was used in the subsequent step without further purification.

$^1$H-NMR (200 MHz, DMSO-d$_6$): δ (ppm): 7.48–7.18 (m, 4H); 4.80–4.41 (m, 2H); 3.82–3.52 (m, 1H); 3.61–3.47 (m, 3H); 2.48–1.80 (m, 4H).

EXAMPLE 21

1-(S)-1-(2-chlorobenzyl)-5-[2-(R)-oxyranyl]-2-pyrrolidinone (Compound No. 25)

Sodium hydride 80% in oil (7.4 g; 247 mmol) was added portionwise to a solution of compound No. 24 (68.4 g; 206 mmol) in dimethylformamide (320 ml) under stirring at 0° C.

The solution was stirred at room temperature for 3 hours, poured into water at 4° C. (1600 ml) and extracted with ethyl ether (3×350 ml).

The organic phase was washed with water (300 ml), dried with sodium sulfate and evaporated at reduced pressure.

The solid residue was crystallized from isopropyl ether (1000 ml).

Compound No. 25 (42.3 g) was obtained as a white solid.

m.p. 75°–76° C.

$[α]^{20}_D = +80.2°$ (c=1.7%-ethanol)

$^1$H-NMR (200 MHz, CDCl$_3$): δ (ppm): 7.37–7.11 (m, 4H); 5.00–4.47 (m, 2H); 3.18–3.08 (m, 1H); 2.92–2.85 (m, 1H); 2.72–2.36 (m, 4H); 2.27–1.81 (m, 2H).

EXAMPLE 22

1-(S)-[1-(2-chlorobenzyl)-2-oxo-5-(S)-pyrrolidinyl]-2-di-(R,R)-sec.butylaminoethanol (Compound No. 26)

A solution of compound No. 25 (15.4 g; 61 mmol) and (R,R)-di-sec.butylamine (8.1 g; 63 mmol) in n-butanol (50 ml) was refluxed for 140 hours.

Then the solvent was evaporated at reduced pressure.

The residue was collected with ethyl ether (200 ml) and extracted with hydrochloric acid 5% (200 ml).

The aqueous phase was decolorated with charcoal, basified at pH 10 with potassium carbonate and extracted with ethyl ether (200 ml).

The ethereal phase was dried on sodium sulfate, evaporated at reduced pressure and the residue was crystallized from hexane (50 ml).

Compound No. 26 (17.1 g) was obtained as a white solid.

m.p. 72°–73° C.

$[α]^{20}_D = -64.6°$ (c=1%-methanol)

$^1$H-NMR (200 MHz, CDCl$_3$): δ (ppm): 7.36–7.12 (m, 4H, Ar); $υ_A$=4.92–$υ_B$=4.63 (AB system, J$_{AB}$=15.6 Hz); 4.00 (broad signal, 1H, OH); 3.66–3.54 (m, 2H, CH—CH); 2.60–1.80 (m, 8H, NCO—CH$_2$—CH$_2$ and CH$_2$—N—CH$_2$); 1.45–1.12 (m, 4H, 2CH$_2$—CH$_3$); 1.80 (d, 6H, J$_{HH}$=6.4 Hz, 2CH$_3$—CH); 0.84 (t, 6H, J$_{HH}$=7.1 Hz, 2CH$_3$—CH$_2$).

EXAMPLE 23

1-(S)-[1-(2-chlorobenzyl)-2-oxo-5-(S)-pyrrolidinyl]-2-dimethylaminoethanol (Compound No. 27)

A solution of compound No. 24 (3.3 g; 10 mmol) and dimethylamine (0.99 g; 22 mmol) in ethanol (15 ml) was stirred at room temperature for 24 hours.

The solvent was evaporated at reduced pressure. The residue was collected with water (30 ml), basified at pH 10 with sodium carbonate and extracted with ethyl acetate (30 ml).

The organic phase was washed with water (15 ml), dried on sodium sulfate and evaporated under vacuum to give a residue which was crystallized from isopropyl ether (12 ml).

Compound No. 27 (2.61 g) was obtained as a white solid.

m.p. 74°–75° C.

$[α]^{20}_D = +3.9°$ (c=1%-methanol)

$^1$H-NMR (200 MHz, CDCl$_3$): δ (ppm): 7.35–7.11 (m, 4H, Ar); $υ_A$=4.93–$υ_B$=4.60 (AB system, J$_{AB}$=15.7 Hz); 3.77 (broad signal, 1H, OH); 3.74–3.64 (m, 1H, CHOH); 3.58–3.50 (m, 1H, CHN); 2.55–2.28 (m, 2H, CH$_2$CO); 2.25–1.74 (m, 4H, CH$_2$N and —COCH$_2$—CH$_2$); 2.16 (s, 6H, (CH$_3$)$_2$N).

By working in a similar way the following compound was prepared:

1-(S)-[1-(2-chlorobenzyl)-2-oxo-5-(S)-pyrrolidinyl]-2-(1-piperidyl)-ethanol (Compound No. 28)

starting from compound No. 24 and piperidine

86% yield-thick oil $[α]^{20}_D = -7.3°$ (c=1%-methanol)

$^1$H-NMR (200 MHz, DMSO-d$_6$): δ (ppm): 7.33–7.10 (m, 4H); 5.00–4.56 (m, 2H); 3.76–3.66 (m, 1H); 3.57–3.47 (m, 1H); 2.55–2.36 (m, 4H); 2.26–1.71 (m, 6H); 1.57–1.32 (m, 6H).

EXAMPLE 24

1-(R)-[1-benzyl-2-oxo-5-(S)-pyrrolidinyl]-1,2-isopropylidene ethanediol (Compound No. 29)

It was prepared as described in example 12 starting from compound No. 14.

67% yield-light yellow oil $^1$H-NMR (200 MHz, DMSO-d$_6$): δ (ppm): 7.38–7.20 (m, 5H); 4.85–4.25 (m, 2H); 4.17–3.40 (m, 4H); 2.45–1.44 (m, 4H); 1.25 (s, 3H); 1.23 (s, 3H).

EXAMPLE 25

1-(R)-[1-benzyl-2-oxo-5-(S)-pyrrolidinyl]-ethanediol (Compound No. 30)

It was prepared as described in example 13 starting from compound No. 29.

84% yield-white solid m.p. 69°–71° C. (ethyl acetate)

$[α]^{20}_D = +100°$ (c=2%-ethanol)

$^1$H-NMR (200 MHz, DMSO-d$_6$): δ (ppm): 7.36–7.16 (m, 5H); 4.91 (d, 1H, J$_{HH}$=5.1 Hz); 4.90–4.15 (m, 2H); 4.47 (t, 1H, J$_{HH}$=5.4 Hz); 3.65–3.55 (m, 1H); 3.51–3.42 (m, 1H); 3.38–3.32 (m, 2H); 2.44–2.09 (m, 2H); 2.02–1.75 (m, 2H).

EXAMPLE 26

1-(R)-[1-benzyl-2-oxo-5-(S)-pyrrolidinyl]-2-bromoethanol (Compound No. 31)

It was prepared as described in example 20 starting from compound No. 29.

90% yield-light yellow oil $^1$H-NMR (200 MHz, DMSO-d$_6$): δ (ppm): 7.40–7.18 (m, 5H); 4.81–4.22 (m, 2H); 3.86–3.76 (m, 1H); 3.57–3.40 (m, 3H); 2.43–1.73 (m, 4H).

EXAMPLE 27

(5S)-1-benzyl-5-[2-(R)-oxyranyl]-2-pyrrolidinone (Compound No. 32)

It was prepared as described in example 21 starting from compound No. 31.

87% yield-white solid $[\alpha]^{20}_D = +121.7°$ (c=2%-ethanol)

$^1$H-NMR (200 MHz, CDCl$_3$): δ (ppm): 7.37–7.18 (m, 5H); 5.00–4.23 (m, 2H); 3.10–3.00 (m, 1H); 2.91–2.84 (m, 1H); 2.76–2.71 (m, 1H); 2.61–2.31 (m, 3H); 2.19–1.74 (m, 2H).

EXAMPLE 28

1-(S)-[1-benzyl-2-oxo-5-(S)-pyrrolidinyl]-2-di-(R,R)-sec.butylaminoethanol (Compound No. 33)

It was prepared as described in example 22 starting from compound No. 32.

70% yield-white solid m.p. 54°–55° C. (hexane)

$[\alpha]^{20}_D = -57.6°$ (c=2%-ethanol)

$^1$H-NMR (200 MHz, CDCl$_3$): δ (ppm): 7.34–7.16 (m, 5H); 4.86–4.46 (m, 2H); 4.07 (broad signal, 1H, OH); 3.62–3.48 (m, 2H); 2.53–2.25 (m, 5H); 2.16–1.70 (m, 3H); 1.46–1.12 (m, 4H); 0.87 (d, 6H, $J_{HH}$=6.5 Hz); 0.84 (t, 6H, $J_{HH}$=7.1 Hz).

EXAMPLE 29

(4R,5S)-N-(2-methoxybenzyl)-4-methanesulonyloxy-5,6-O-isopropylidene-5,6-dihydroxy-hexanamide (Compound No. 34)

It was prepared as described in example 16 starting from compound No. 15.

98% yield-colorless oil $^1$H-NMR (200 MHz, DMSO-d$_6$): δ (ppm): 8.20 (m, 1H); 7.28–6.84 (m, 4H); 4.72–4.65 (m, 1H); 4.31–4.18 (m, 3H); 4.08–3.71 (m, 2H); 3.79 (s, 3H); 3.20 (s, 3H); 2.36–2.27 (m, 2H); 2.02–1.70 (m, 2H); 1.34 (s, 3H); 1.26 (s, 3H).

EXAMPLE 30

1-(R)-[1-(2-methoxybenzyl)-2-oxo-5-(S)-pyrrolidinyl]-1,2-isopropylidene-ethandiol (Compound No. 35)

It was prepared as described in example 17 starting from compound No. 34.

83% yield-light yellow oil $^1$H-NMR (200 MHz, DMSO-d$_6$): δ (ppm): 7.28–6.82 (m, 4H); 4.70–4.36 (m, 2H); 4.18–4.10 (m, 1H); 3.97–3.44 (m, 3H); 3.79 (s, 3H); 2.45–1.50 (m, 4H); 1.20 (s, 6H).

EXAMPLE 31

(5S)-1-(2-methoxybenzyl)-5-[2-(R)-oxyranyl]-2-pyrrolidinone (Compound No. 36)

It was prepared as described in examples 20 and 21 starting from compound No. 35.

77% yield-white solid m.p. 91°–93° C. (isopropyl ether)

$[\alpha]^{20}_D = +88.1°$ (c=2%-ethanol)

$^1$H-NMR (200 MHz, CDCl$_3$): δ (ppm): 7.24–6.80 (m, 4H, Ar); $v_A$=4.88–$v_B$=4.37 (AB system, $J_{AB}$=15.6 Hz, CH$_2$—Ar); 3.80 (s, 3H, OCH$_3$); 3.25–3.14 (m, 1H, N—CH—CH$_2$); 2.97–2.95 (m, 1H, NCH—CH); 2.71–2.30 (m, 4H, NCOCH$_2$ and NCHCH—CH$_2$); 2.20–1.76 (m, 2H, NCOCH$_2$—CH$_2$).

EXAMPLE 32

1-(S)-[1-(2-methoxybenzyl)-2-oxo-5-(S)-pyrrolidinyl]-2-di-(R,R)-sec.butylaminoethanol (Compound No. 37)

It was prepared as described in example 22 starting from compound No. 36.

78% yield-white solid m.p. 77°–79° C. (isopropyl ether)

$[\alpha]^{20}_D = -63.1°$ (c=1%-methanol)

$^1$H-NMR (200 MHz, CDCl$_3$): δ (ppm): 7.24–6.80 (m, 4H, Ar); $v_A$=4.81–$v_B$=4.42 (AB system, $J_{AB}$=15.3 Hz, CH$_2$—Ar); 3.84 (broad signal, 1H, OH); 3.80 (s, 3H, OCH$_3$); 3.74–3.63 (m, 2H, CH—CH); 2.55–1.80 (m, 8H, NCOCH$_2$CH$_2$ and CH$_2$—N—CH$_2$); 1.45–1.12 (m, 4H, CH$_2$—CH$_3$); 0.88 (d, 6H, $J_{HH}$=6.2 Hz, 2CH$_3$—CH); 0.83 (t, 6H, $J_{HH}$=7 Hz, 2CH$_3$—CH$_2$).

What we claim is:

1. A stereoselective process for the preparation of any stereoisomer of the compounds of formula

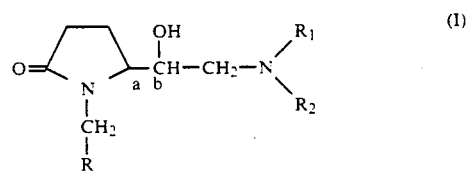

wherein

R is a phenyl optionally substituted by from 1 to 3 substituents selected from the class consisting of C$_1$–C$_4$ alkyl, C$_1$–C$_4$ alkoxy, hydroxy, halogen, and CF$_3$;

R$_1$ and R$_2$, which may be the same or different, are a linear or branched C$_1$–C$_6$ alkyl, a C$_3$–C$_6$ cycloalkyl; or R$_1$ and R$_2$, together with the nitrogen atom to which they are bonded, make a 5- or 6-membered heterocycle, which can further contain 1 or 2 heteroatoms selected from the class consisting of oxygen, nitrogen and sulfur, optionally substituted by 1 or 2 C$_1$–C$_4$ alkyl groups; and a and b mark the asymmetric carbon atoms; which process comprises:

the transformation of the compound of formula (II)

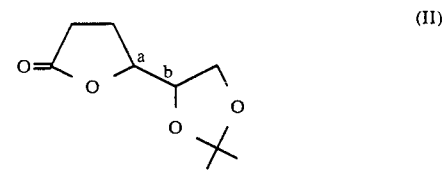

in which a and b have the above reported meanings into the compound of formula (III)

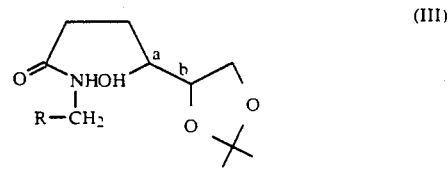

in which R, a and b have the above reported meanings by reaction with a benzylamine of formula RCH$_2$NH$_2$ (VII) in which R has the above reported meanings, with retention of configuration of the carbon atoms a and b;

the subsequent cyclization of the compound of formula (III) into the compound of formula

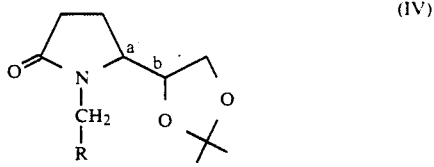
(IV)

in which R, a and b have the above reported meanings; by conversion of the hydroxy group in a into the corresponding mesyl-derivative and subsequent ring closure in a dipolar aprotic solvent and in the presence of a base, with inversion of the configuration of the carbon atom a and retention of the configuration of the carbon atom b;

the hydrolysis of the compound of formula (IV) with an acid, in a solvent or mixture of solvents in order to obtain the compound of formula

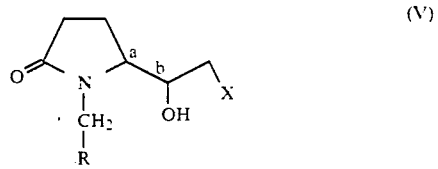
(V)

in which X is a hydroxy or a chlorine or bromine atom and R$_1$, a and b have the above reported meanings, with retention of configuration of the carbon atoms a and b;

the epoxidation of the compound of formula (V) in order to obtain the compound of formula

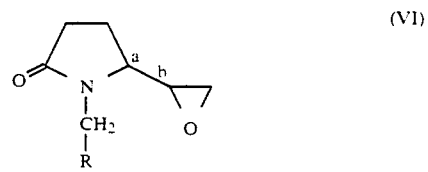
(VI)

in which R$_1$, a and b have the above reported meanings, with retention of configuration of the carbon atoms a and b;

the subsequent reaction of the thus-obtained compound of formula (VI) with a substituted amine of formula HNR$_1$R$_2$ (VIII) in which R$_1$ and R$_2$ have the above reported meanings, in a solvent or mixture of solvents in order to obtain the compound of formula (I), with retention of configuration of the carbon atoms a and b.

2. A process according to claim 1 in which the mesyl-derivative of the compound of formula III is not isolated from the reaction environment but converted into the compound of formula IV.

3. A process according to claim 1 in which the substituted amine VIII is reacted with the epoxide of formula VI in 1:1 molar ratio or with a slight excess of the amine, in order to obtain the compound of formula I with retention of configuration of the carbon atoms a and b.

4. A process according to claim 1 in which the compound of formula V in which X=Br or Cl, is directly treated with the amine VIII in at least a molar amount that is double with respect to that of compound V, in order to obtain the compound of formula I with retention of configuration of the carbon atoms a and b.

5. A stereoisomer of a compound of formula

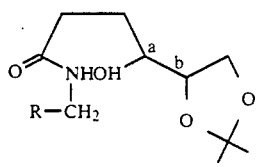
(III)

in which

R is a phenyl optionally substituted by from 1 to 3 substituents selected from the class consisting of C$_1$–C$_4$ alkyl, C$_1$–C$_4$ alkoxy, hydroxy, halogen, CF$_3$;

a and b marking the asymmetric carbon atoms.

6. A stereoisomer of a compound of formula

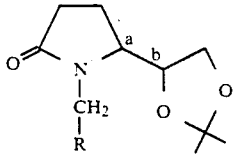
(IV)

in which

R is a phenyl optionally substituted by from 1 to 3 substituents selected from the class consisting of C$_1$–C$_4$ alkyl, C$_1$–C$_4$ alkoxy, hydroxy, halogen, CF$_3$;

a and b marking the asymmetric carbon atoms.

* * * * *